United States Patent [19]
Moberly

[11] Patent Number: 5,974,606
[45] Date of Patent: Nov. 2, 1999

[54] CPR BACKBOARD AND METHOD OF USE

[76] Inventor: Jeffrey Moberly, 6686 Navilleton Rd., Floyds Knobs, Ind. 47119

[21] Appl. No.: 08/960,021

[22] Filed: Oct. 29, 1997

Related U.S. Application Data

[63] Continuation of application No. 08/769,401, Dec. 19, 1996, Pat. No. 5,806,377.

[51] Int. Cl.⁶ .................................................. A47C 31/00
[52] U.S. Cl. ...................................... 5/630; 5/658; 5/728
[58] Field of Search ........................... 5/630, 658, 501.1, 5/659, 626, 628, 81.45, 424, 625, 728; 128/870, 869, 871

[56] References Cited

U.S. PATENT DOCUMENTS

| | | |
|---|---|---|
| 1,663,103 | 3/1928 | Thompson . |
| 2,490,867 | 12/1949 | Greenhill . |
| 2,607,050 | 8/1952 | Binschoff ................................ 5/81.1 R |
| 3,003,164 | 10/1961 | Calvelage ................................ 128/870 |
| 3,535,719 | 10/1970 | Murcott ........................................ 5/424 |
| 4,048,681 | 9/1977 | Baulch et al. ........................... 5/81.1 R |
| 4,237,914 | 12/1980 | Gantz ........................................... 5/424 |
| 4,369,982 | 1/1983 | Hein et al. . |
| 4,729,138 | 3/1988 | Heyman et al. ............................. 5/424 |
| 4,807,313 | 2/1989 | Ryder et al. . |
| 4,979,520 | 12/1990 | Boone, Jr. et al. . |
| 4,993,092 | 2/1991 | Weeks . |
| 5,473,784 | 12/1995 | Nixon et al. . |

*Primary Examiner*—Michael F. Trettel
*Assistant Examiner*—Fredrick Conley
*Attorney, Agent, or Firm*—Middleton & Reutlinger; Charles G. Lamb

[57] ABSTRACT

A CPR backboard is provided with a pair of straps disposed on opposite ends of the backboard, the straps being attached to hooks attachable to a bed frame. The straps are provided with adjustable self-locking buckles. In use, a mattress is placed between the backboard and a bed frame with the opposed hooks hooking opposite sides of the bed frame with the mattress disposed therebetween. The straps are adjustable to compress the mattress between the backboard and the bed frame with the self-locking buckle maintaining the straps at a preselected compressing position thereby providing for a firm surface on which chest compressions can be performed upon a patient.

14 Claims, 2 Drawing Sheets

CPR BACKBOARD AND METHOD OF USE

CROSS REFERENCE TO RELATED APPLICATION

This is a continuation application of Ser. No. 08/769,401 filed Dec. 19, 1996, now U.S. Pat. No. 5,806,377.

BACKGROUND OF THE INVENTION

This invention relates to a CPR backboard and particularly to a CPR backboard mounted onto a mattress and bed frame.

In a hospital setting when external chest compressions, or CPR, is performed, a patient is generally placed onto a backboard made of wood, plastic or other material, the backboard being placed upon a mattress in a position to receive the back of the patient. The backboard is approximately the width of a bed in a longitudinal direction and wide enough to receive the entire back of a patient in a latitudinal direction. The backboard provides a relatively firm surface for performing chest compressions. However, even though the backboard provides a firmer surface than a mattress alone, there is still considerable bounce in the patient due to the compressing and expansion of the mattress as the chest compressions are being performed.

SUMMARY OF THE INVENTION

It is an object of the present invention to increase the firmness of a surface upon which a patient lies when chest compressions are performed.

It is another object of the present invention to provide a CPR backboard that increases the ease of administration and effectiveness in the performance of chest compressions.

It is even another object of the present invention to provide an apparatus which reduces the bounce when chest compressions are performed in a hospital setting.

It is even a further object of the present invention to provide an apparatus for use for chest compressions which is easy to use and convenient.

It is an even further object of the present invention to provide an apparatus which may be set up quickly and be in performance with hospital codes for performing CPR.

It is also an object of the present invention to provide a CPR backboard with means to compress a mattress between the backboard and the bed frame thereby increasing the firmness in performing chest compressions.

More particularly, the present invention provides a CPR backboard comprising a backboard and a pair of adjustable bed frame hook means attached on opposite sides of the backboard.

Accordingly, other objects, features and advantages of the present invention will be apparent to those skilled in the art by reference to the following description of preferred embodiments, drawings, and claims.

DETAILED DESCRIPTION OF THE PREFERRED EMBODIMENTS

Figure 1:
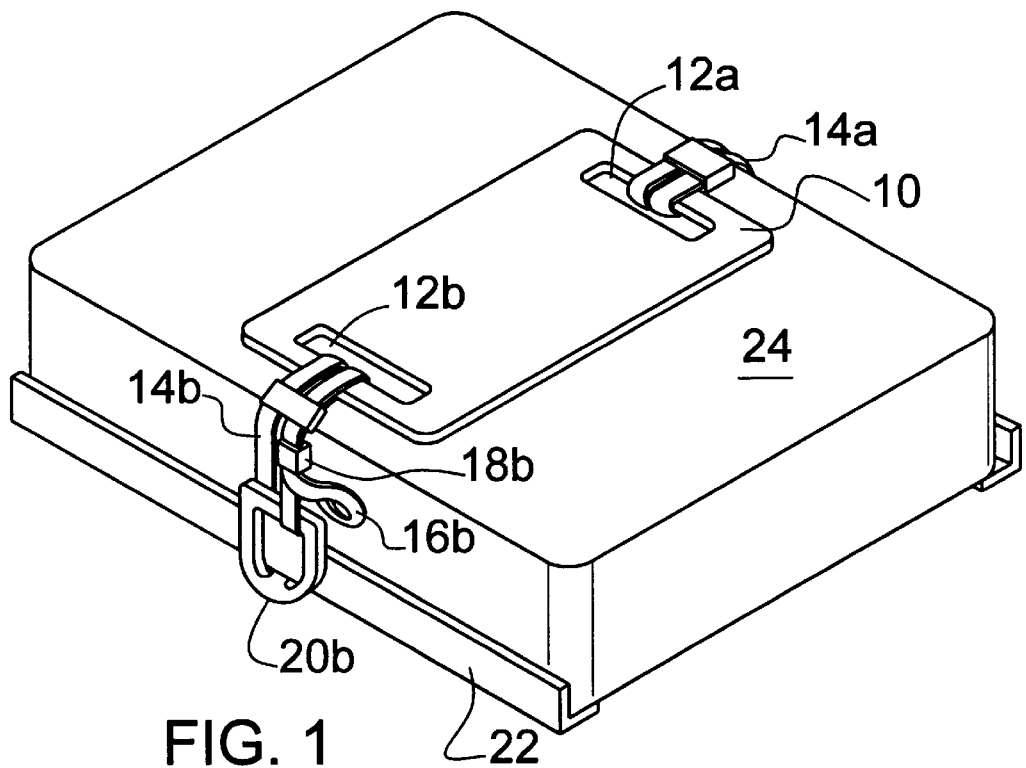
FIG. 1 is a perspective view of one preferred backboard of the present invention in combination with a mattress and a bed frame.
Figure 2:
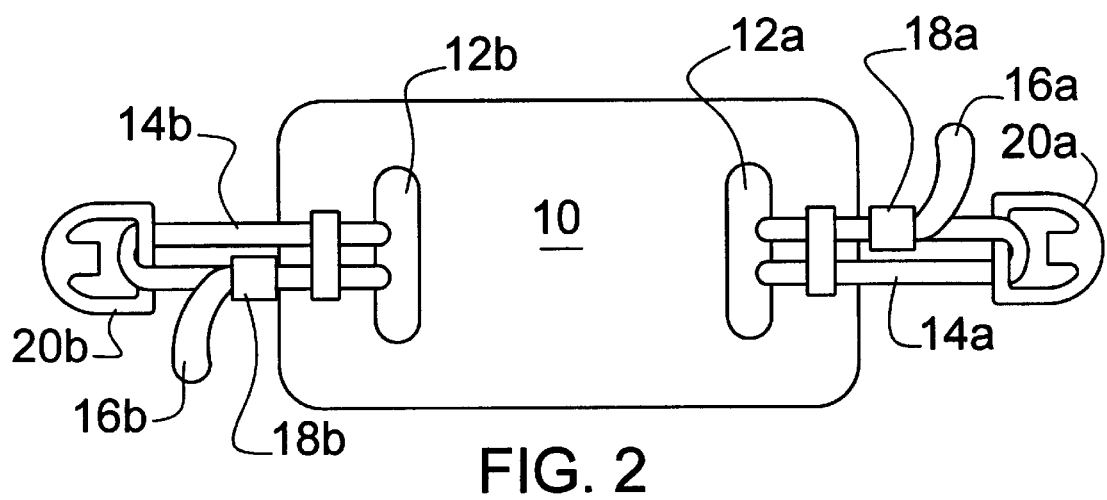
FIG. 2 is a top view of a CPR backboard of the present invention.
Figure 3:
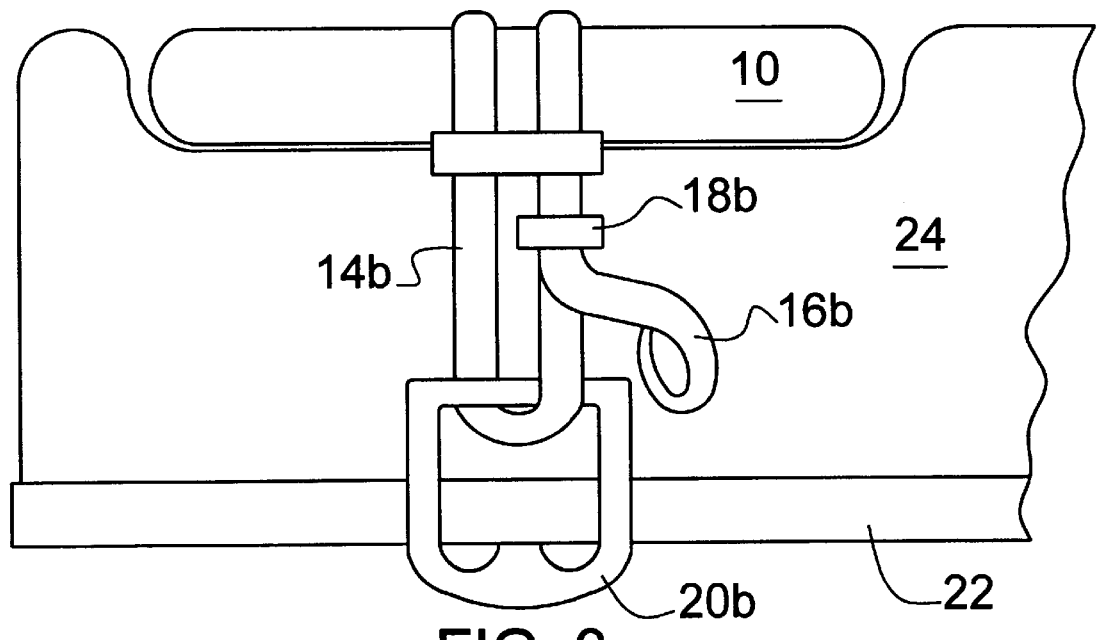
FIG. 3 is side view of the CPR backboard of FIG. 1.

Referring now to the drawings, as best shown in FIG. 1, a backboard 10 is provided with a pair of slots 12a and 12b on opposite ends of the backboard 10, the slots 12a and 12b being used as handles for the backboard 10 as well as receiving straps 14a and 14b which are looped through the slots 12a and 12b, respectively. Also, straps 14a, 14b are looped through bed frame hook devices 20a and 20b, respectively, as best shown in FIGS. 2 and 3. Moreover, the straps 14a and 14b are received by adjustable self-locking strap buckles 18a and 18b, respectively, which provide means for adjusting the length of the straps 14a and 14b which in turn adjusts the distances between the hooks 20a, 20b and the CPR backboard 10 with a mattress 24 disposed therebetween. The straps 14a and 14b terminate in handles 16a and 16b, respectively.

Referring to FIGS. 1 and 3, the CPR backboard 12 is placed upon the mattress 24 and the hook means 20a (FIG. 2) and 20b are attached to the bed frame supports 22. The hook means 20a and 20b are hooked under the bed frame supports 22 with the strap handles 16a and 16b being pulled tight as shown in FIG. 3 so that the mattress is compressed between the backboard 10 and the bed frame supports 22. As soon as the straps 14a and 14b have been tightened, adjustable self-locking buckles 18a and 18b hold the straps 14a and 14b in a locking position thereby maintaining the mattress 24 in a compressed state. The patient upon which the chest compressions is to be performed may then be placed upon the CPR backboard 10 and the chest compressions performed.

Figure 4:
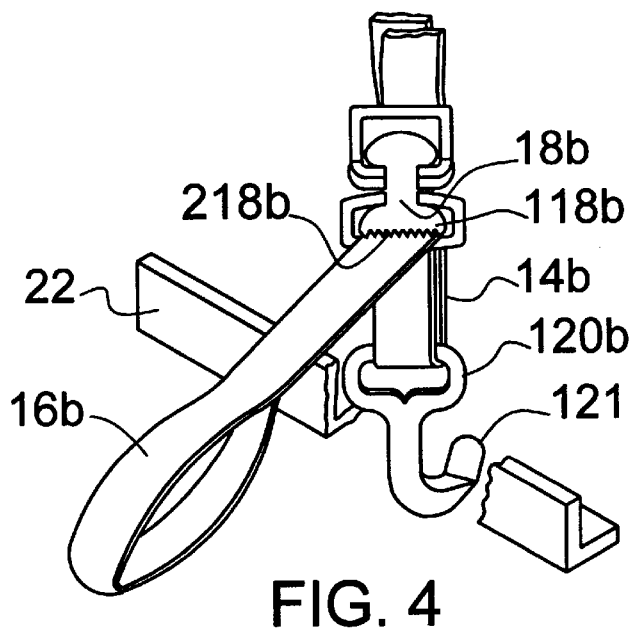
FIG. 4 is a perspective view, with selected portions cut-away, of another preferred bed frame hook and an adjustable self-locking strap buckle of the present invention.

As shown in FIG. 4, a J-shaped hook identified by the numeral 120b, may also be used in the present invention. In the J-shaped hook, 120b, the terminating end 121 engages with an extends underneath the bed frame support 22. And, adjustable self-locking buckle 18b includes a self-locking spring clip 118b having outwardly extending teeth 218b engageable with strap 14b.

It is realized that only one strap means has been shown for the compression of a mattress 24 between the backboard 10 and a bed frame support 22, but other strapping means may be utilized. Also, it is realized that adjustable self-locking buckles identified by the numerals 18a and 18b are commercially available for use in the present invention and those including spring clips therein for locking the straps in a set condition once the straps have been pulled through the buckles 18a and 18b, are preferred.

It is realized that other variations and modifications of the preferred embodiment are possible without departing from the scope and spirit of the present invention. And, it is not intended that the aforementioned discussion in any way limits the scope of the present invention as set forth in the appended claims.

What is claimed is:

1. In combination with a mattress and a bed frame, a CPR backboard comprising:

a backboard;

a pair of adjustable straps attached to opposite ends of said backboard; and, a pair of bed frame hooks, each of said bed frame hooks being attached to each of said straps and in hooking relation with said bed frame, said mattress being disposed between said CPR backboard and said bed frame, said CPR backboard being of unitary construction and lying flat upon said mattress, said straps and said hooks being in cooperating relation to adjust the thickness of said mattress.

2. The backboard of claim 1, said backboard including handles.

3. The backboard of claim 2, said handles being a pair of elongated slots on opposite ends of said backboard.

4. The backboard of claim 3, each of said straps looping through one of said elongated slots.

5. The backboard of claim 4, each of said bed frame hooks including a strap receiving slot therein, each of said straps being looped through said strap receiving slot.

6. The backboard of claim 5, said hook being of J-shaped configuration with a terminating end engageable with and extendable beneath a bed frame support.

7. The backboard of claim 1, each of said straps including an adjustable self-locking buckle.

8. A method for preparing an apparatus for performing CPR comprising the steps of:

placing a backboard onto a mattress resting on a bed frame, said backboard including a pair of adjustable straps on opposite sides of said backboard, each of said adjustable straps being attached to bed frame hook;

hooking said bed frame hook to opposing sides of said bed frame;

tightening said adjustable straps thereby compressing said mattress between said backboard and said bed frame; and, placing a patient upon which chest compressions are to be performed upon said backboard.

9. The method of claim 8, said backboard including handles.

10. The method of claim 9, said handles being a pair of elongated slots on opposite ends of said backboard.

11. The method of claim 10, each of said straps looping through each of said elongated slots.

12. The method of claim 11, said bed frame hook including a strap receiving slot therein, one of said straps being looped through said strap receiving slot.

13. The method of claim 12, said hook being of J-shaped configuration with a terminating end engageable with and extendable beneath a bed frame support.

14. The method of claim 8, each of said straps including an adjustable self-locking buckle.

* * * * *